(12) United States Patent
Bhamla et al.

(10) Patent No.: US 9,265,413 B2
(45) Date of Patent: Feb. 23, 2016

(54) I-DDROP: INTERFACIAL DEWETTING AND DRAINAGE OPTICAL PLATFORM

(71) Applicant: The Board of Trustees of the Leland Stanford Junior University, Palo Alto, CA (US)

(72) Inventors: Mohammed Saad Bhamla, Stanford, CA (US); Gerald G. Fuller, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/512,304

(22) Filed: Oct. 10, 2014

(65) Prior Publication Data

US 2015/0103315 A1    Apr. 16, 2015

Related U.S. Application Data

(60) Provisional application No. 61/889,943, filed on Oct. 11, 2013.

(51) Int. Cl.
*A61B 3/14* (2006.01)
*G02C 5/00* (2006.01)
*G02C 7/00* (2006.01)
*A61B 3/10* (2006.01)

(52) U.S. Cl.
CPC ..................................... *A61B 3/101* (2013.01)

(58) Field of Classification Search
CPC .......... A61B 3/14; A61B 3/103; A61B 3/113; A61B 3/125; A61B 3/1225; A61B 3/024; A61B 3/032; A61B 3/1015; G02C 5/00; G02C 7/02; G02C 7/04
USPC ................. 351/206, 200, 205, 209–210, 219, 351/221–223, 41, 159.01, 159.02, 246
See application file for complete search history.

(56) References Cited

U.S. PATENT DOCUMENTS

2012/0271555 A1* 10/2012 Levental ............. A61B 5/0057
702/19

OTHER PUBLICATIONS

Lin et al. Contact Lenses Wettability in Vitro: Effect of Surface-Active Ingredients. Optometry and Vision Science, Vol. 87, No. 6, pp. 440-447 (2010).
Millar et al. The surface activity of purified ocular mucin at the air-liquid interface and interactions with meibomian lipids. Cornea. Jan. 2006;25(1):91-100.

* cited by examiner

*Primary Examiner* — Dawayne A Pinkney
(74) *Attorney, Agent, or Firm* — Lumen Patent Firm

(57) ABSTRACT

An interfacial dewetting and drainage optical platform (i-DDrOP) is provided which is an instrument that can quantify drainage and dewetting processes of in vitro model tear films covering contact lenses.

1 Claim, 16 Drawing Sheets

Drainage Dynamics

Modeling Drainage Flow using Thin-Film Equations

Governing Equations:

Momentum  $\mu \dfrac{\partial^2 u}{\partial y^2} = -\rho g \sin\theta$

Mass  $\dfrac{\partial h}{\partial t} = -\dfrac{1}{R\sin\theta}\dfrac{\partial}{\partial \theta}(\underbrace{Q\sin\theta}_{\text{volume flux}})$

Boundary Conditions:

No-slip  $u|_{y=0} = 0$

Kinematic  $u|_{y=h} = u_s(\theta, t)$

Tangential Stress  $\dfrac{\partial u}{\partial y}\bigg|_{y=h} = \dfrac{2\mu_s}{\mu R^2}\nabla_s^2 u_s = \dfrac{2\mathbf{Bq}}{h_0}\nabla_s^2 u_s$

---

$\dfrac{\partial h}{\partial t} + \alpha \dfrac{\rho g}{\mu R \sin\theta}\dfrac{\partial}{\partial \theta}(h^3 \sin^2\theta) = 0$ $Bq \to 0$ : Zero interfacial viscosity ($\alpha = 1/3$)
$Bq \to \infty$ : Infinite interfacial viscosity ($\alpha = 1/12$)

Asymptotic Limiting Cases:

$$\boxed{H(\theta = 0, \tau) = \dfrac{1}{\sqrt{1 + 4\alpha\tau}}}$$

$H = \dfrac{h}{h_0} \qquad \tau = \dfrac{t}{\dfrac{\mu R}{\rho g h_0^2}}$

FIG. 4

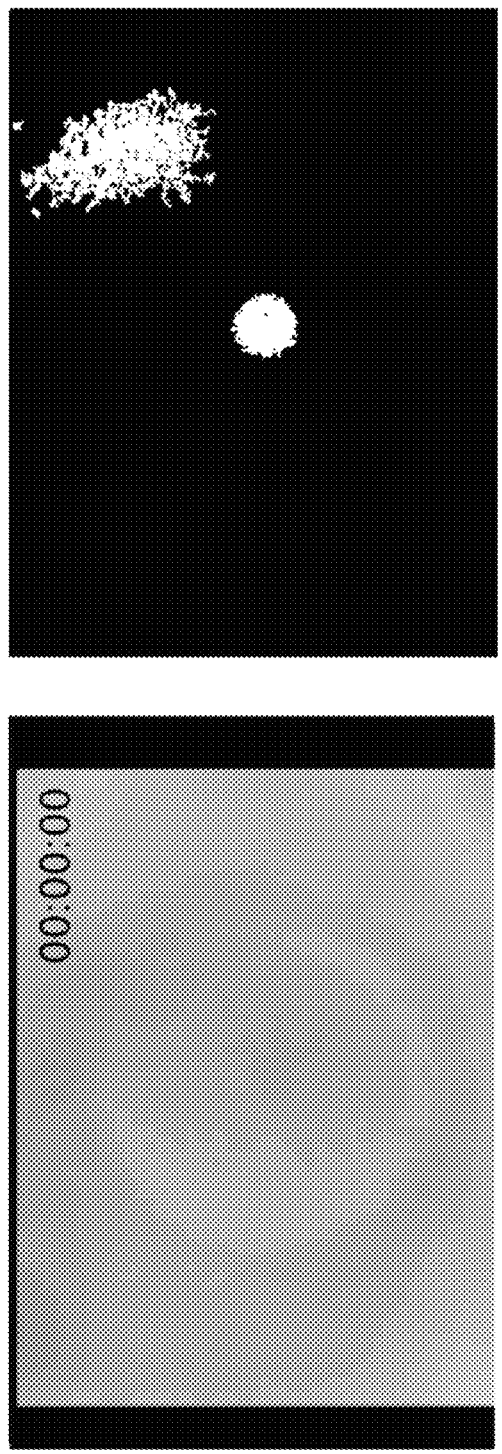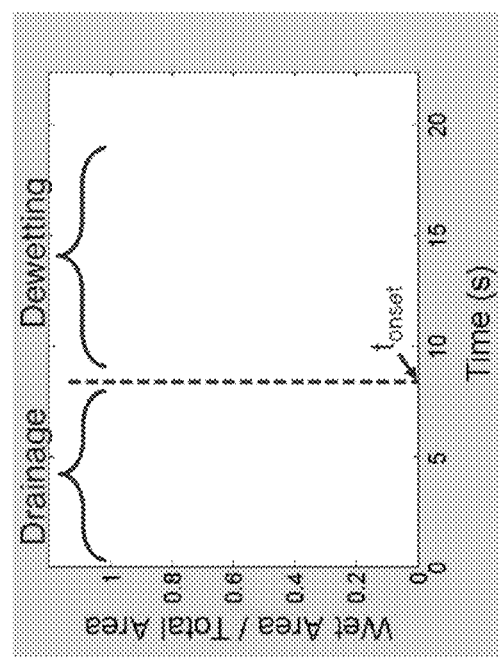
FIG. 10A

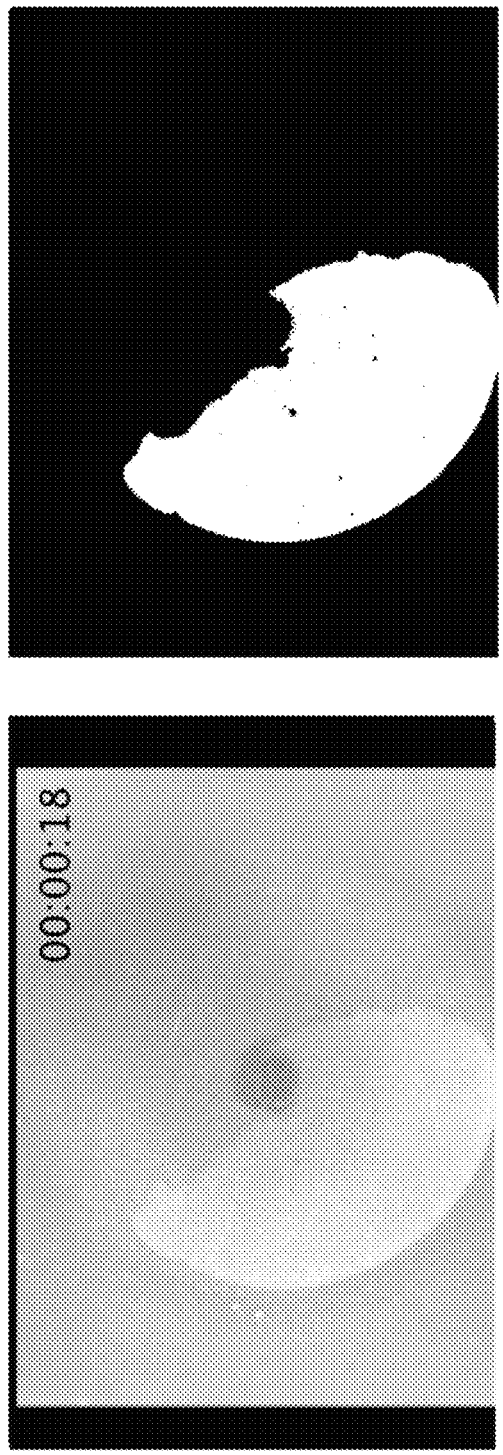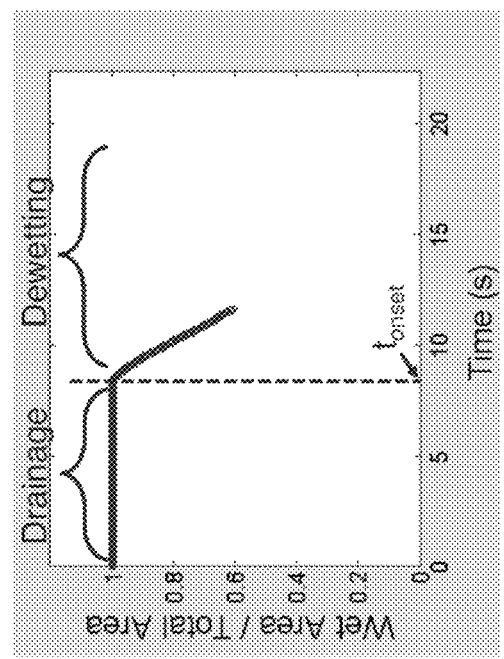
FIG. 10B
AirOptix (Lotrafilcon B) with deionized water.

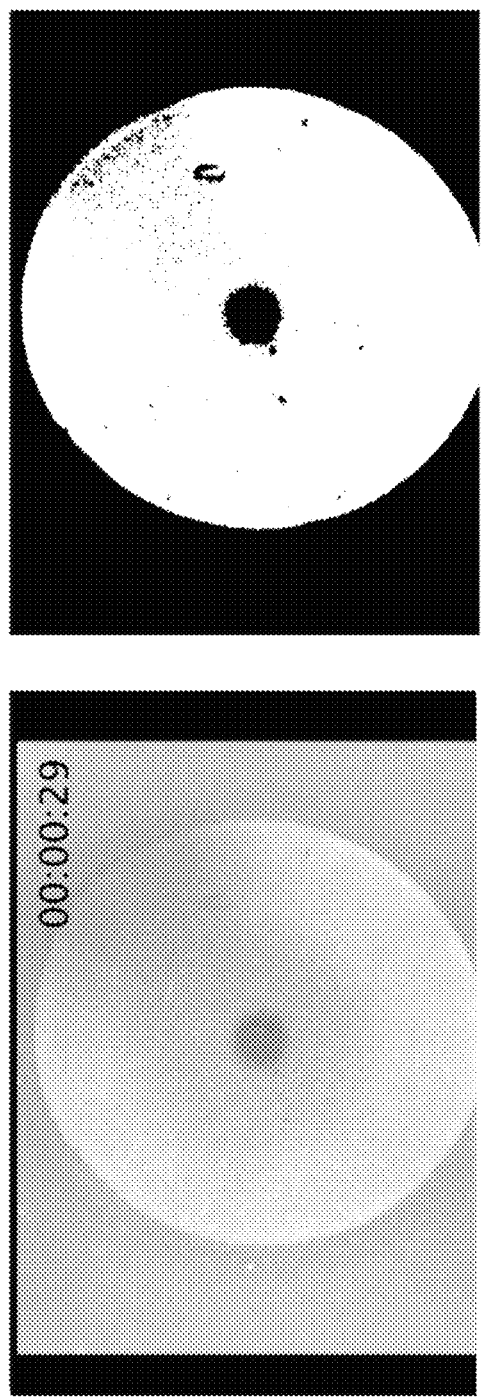
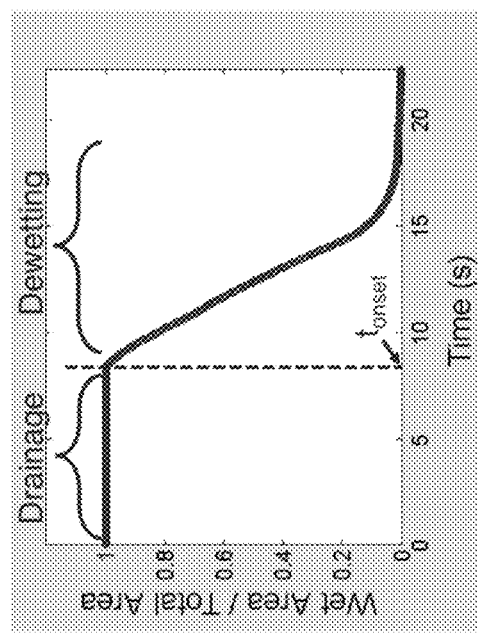
AirOptix (Lotrafilcon B) with deionized water.
FIG. 10C

1110 = Water
1120 = DPPC
1130 = Meibum

I-DDROP: INTERFACIAL DEWETTING AND DRAINAGE OPTICAL PLATFORM

CROSS-REFERENCE TO RELATED APPLICATIONS

This application claims priority from U.S. Provisional Patent Application 61/889,943 filed Oct. 11, 2013, which is incorporated herein by reference.

FIELD OF THE INVENTION

This invention relates to methods and systems for analyzing or examining the drainage and wettability characteristics of contact lenses and lens care products.

BACKGROUND OF THE INVENTION

Insoluble lipids serve vital functions in our bodies and interact with biomedical devices, e.g. the tear film on a contact lens. Over a period of time, these naturally occurring lipids form interfacial coatings that modify the wettability characteristics of these foreign synthetic surfaces. There is a need in the art to develop methods and system that allow us to examine the deposition and consequences of tear film lipids on for example silicone hydrogel (SiHy) contact lenses.

SUMMARY OF THE INVENTION

The invention pertains to methods and systems for examining the interaction of silicone hydrogel contact lenses with a tear film. The interplay between lenses and a complex multicomponent film is central in the comfort experienced by the user. Endogenous biomolecules, such as proteins, mucins, and meibomian lipids, can absorb onto the lenses and alter their surface wetting characteristics. This fouling can induce instability of the tear film and encourage dewetting and dryness.

The interfacial dewetting and drainage optical platform (i-DDrOP) is an instrument that can quantify drainage and dewetting processes of in vitro model tear films covering contact lenses. In an exemplary embodiment of the invention the measurements by this instrument are:

1. Testing of the wettability characteristics of contact lenses.
2. Testing of the problem of contamination of lenses by naturally occurring tear film proteins and lipids that can diminish the ability of lenses to maintain a stable film.
3. Testing the efficacy of lens care solutions that have been developed to restore lens comfort and diminish the deleterious effect of fouling.
4. Measuring the consequences of imbalances of salt concentrations between lenses and the ocular environment, which is also important to lens comfort.
5. Testing the degradation of the lens surface coatings as a function of normal wear & tear. The degradation of the lens will impact the comfort a user feels over time and can result in inflammatory reactions, bacterial infections and potential discontinuation of the lens product.

In one example, the instrument hardware includes the following elements. A Teflon mini-Langmuir trough is fixed onto a stationary support structure. This trough allows one to spread an insoluble monolayer of material (meibum, phospholipids, cholesterol) on top of an aqueous sub-phase at a controlled surface pressure. Surrounding the trough is a moving platform that can elevate a contact lens (mounted on a dome) from an initial position slightly beneath the interface and send it through the interface at computer-controlled speeds [0.001-25 mm/s]. Attached to the moving platform is a high-speed [e.g. 10 ms] interferometer that acquires data on the thickness of the aqueous layer on the top of the lens as a function of time. The trough is equipped with heating elements on the underside, which enable drainage and dewetting experiments at physiological temperatures (34-37 degrees Celsius). The whole setup is also enclosed in a polycarbonate chamber, which allows for control over variables such as environmental humidity and ambient air temperature during experiments. This capability is useful for simulating dry or humid environment conditions at various ambient temperatures that exist in different geographical locations.

Embodiments of the invention can be used to analyze the wettability characteristics of contact lenses and lens care products.

Specifically, the invention provides a system for analyzing characteristics of a contact lens, which distinguishes the following elements. A Langmuir trough is fixed onto a stationary support structure and allows one to spread an insoluble monolayer of material on top of an aqueous sub-phase at a controlled surface pressure. A spherical titanium dome, supported by a dome holder, capable of supporting the contact lens. A moving platform for elevating the dome holder, while holding the contact lens on top of the spherical titanium dome, from an initial position slightly beneath the interface of the content in the Langmuir trough and sending the contact lens through the content in the Langmuir trough at computer-controlled speeds. An interferometer is used for acquiring thickness data of an aqueous layer on the top of the lens as a function of time (also referred to as the drainage experiments). A CCD camera is used for acquiring video data of the contact lens. A computer executing a computer-implemented code is used for analyzing the acquired video data and outputting wettability characteristics of the contact lens (also referred to as the dewetting experiment). Heating elements provided underneath the trough and a humidity chamber enable measurement at user-defined temperatures and humidity conditions.

The i-DDrOP is a compact bench-top platform that attempts to mimic the tear film dynamics as faithfully as possible. It enables measurement of qualitative and quantitative information for drainage and dewetting that is useful to distinguish different contact lenses, coatings etc. These measurements are useful to predict in vivo comfort and functioning of the lens product. The iDDrOP aims to be a more economic alternative to clinical trials.

BRIEF DESCRIPTION OF THE DRAWINGS

FIG. 4 shows according to an exemplary embodiment of the invention a equations describing the theory for modeling drainage flow.

FIG. 7 also shows the placement of the dome holder as it moves through the trough.

FIG. 10A-C each show according to an exemplary embodiment of the invention snapshots of a dewetting experiment on a contact lens using the i-DDrOP.

FIG. 13A shows the humidity chamber adapted to the interferometer for drainage experiments. FIG. 13B shows the inside of the chamber with sidewalls equipped with heating elements and drawer for silica gel particles to absorb moisture. FIG. 13C shows the humidity chamber adapted to camera and illumination dome for dewetting experiments.

DETAILED DESCRIPTION

Figure 1:
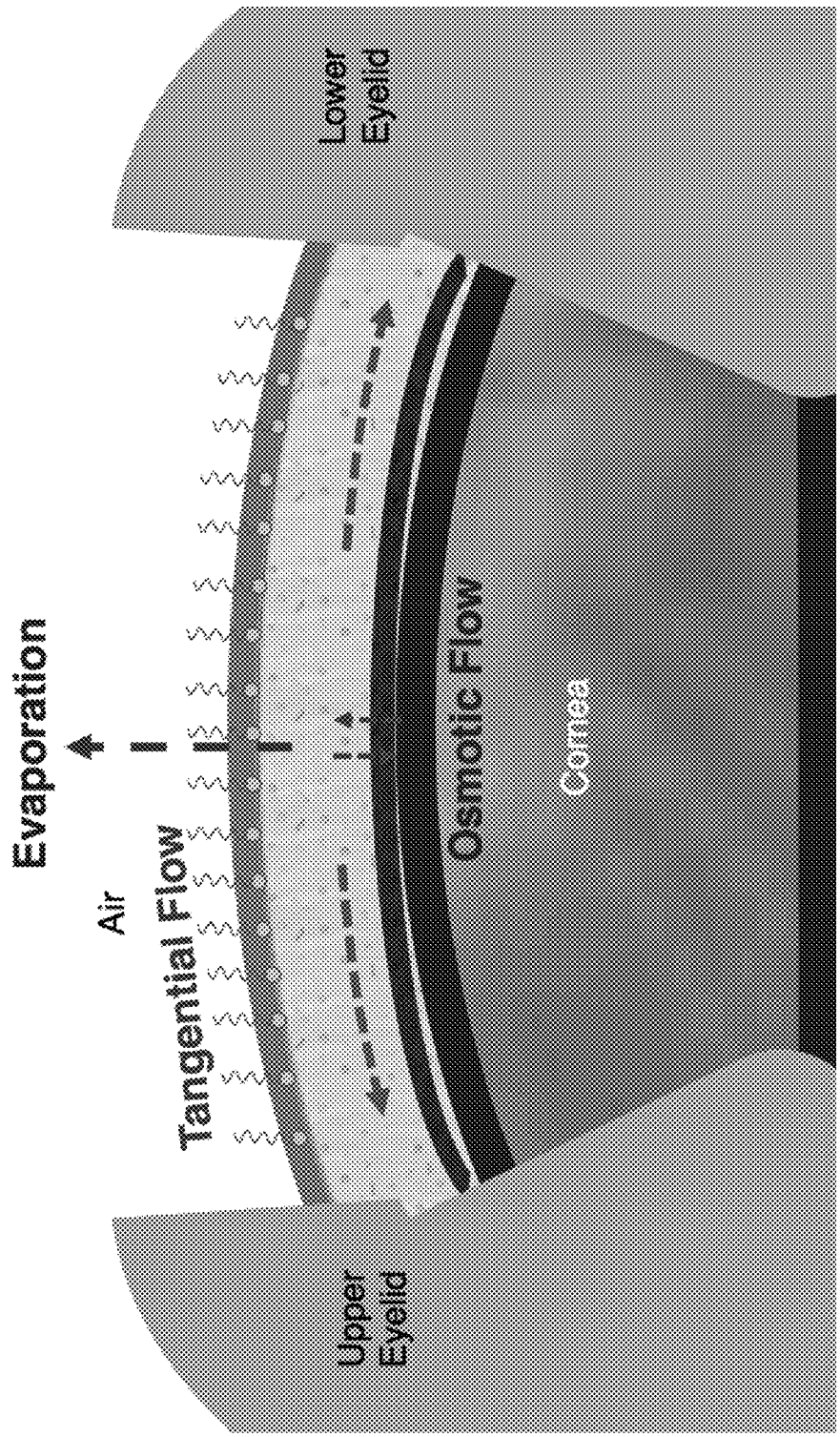
FIG. 1 shows an illustration of the meaning of drainage according to an exemplary embodiment of the invention.

During a blink-cycle on a human eye, there are various processes that occur such as evaporation, osmotic flow and tangential flow. These processes result in the thinning of the tear film, which we refer to as drainage (FIG. 1).

Figure 2:
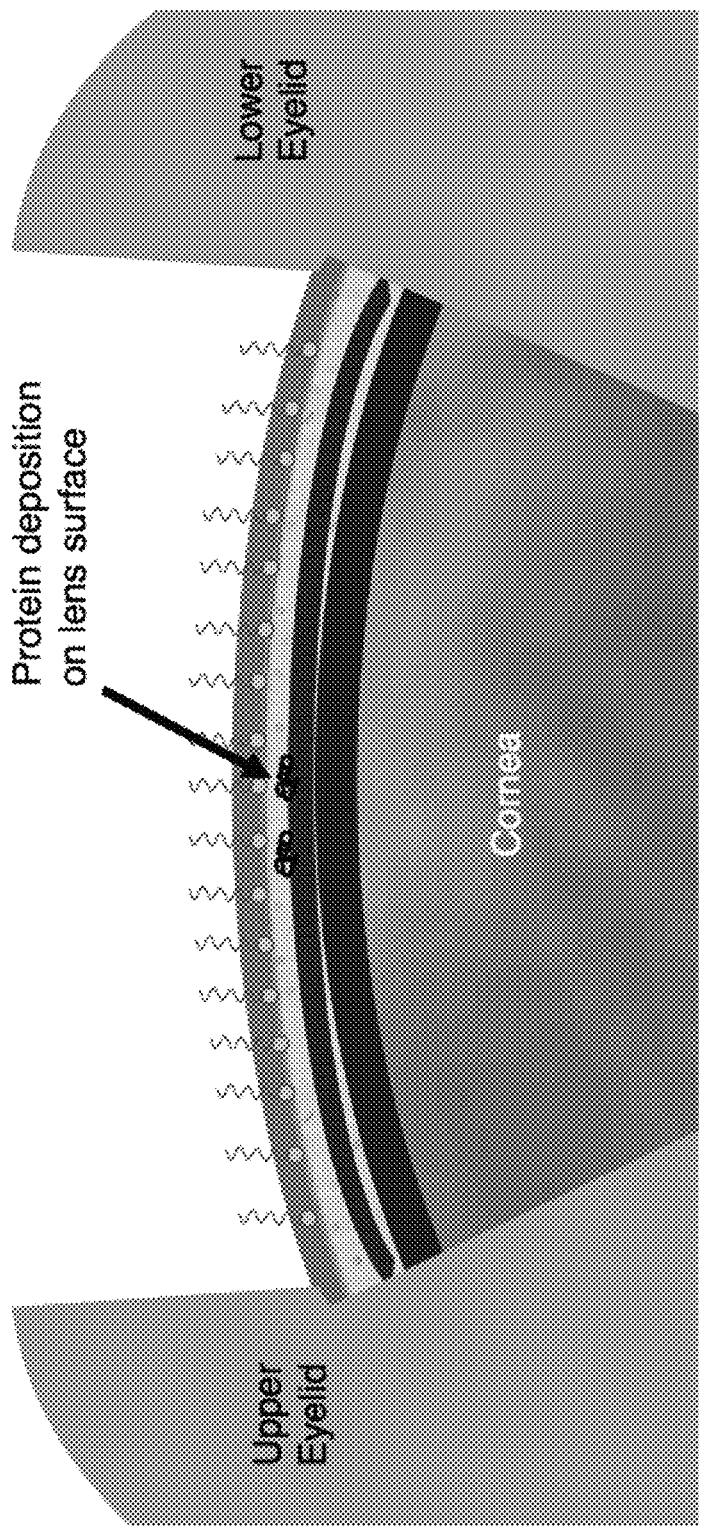
FIG. 2 shows an illustration of the meaning of dewetting according to an exemplary embodiment of the invention.

FIG. 2 illustrates dewetting in the context of i-DDrOP, the Interfacial Dewetting and Drainage Optical Platform of this invention. Once the tear film has drained due to the processes shown in FIG. 1, the tear film breaks up or dewets. This break-up or dewetting is exacerbated when you have naturally occurring tear film proteins depositions on the contact lens surface.

Figure 3:
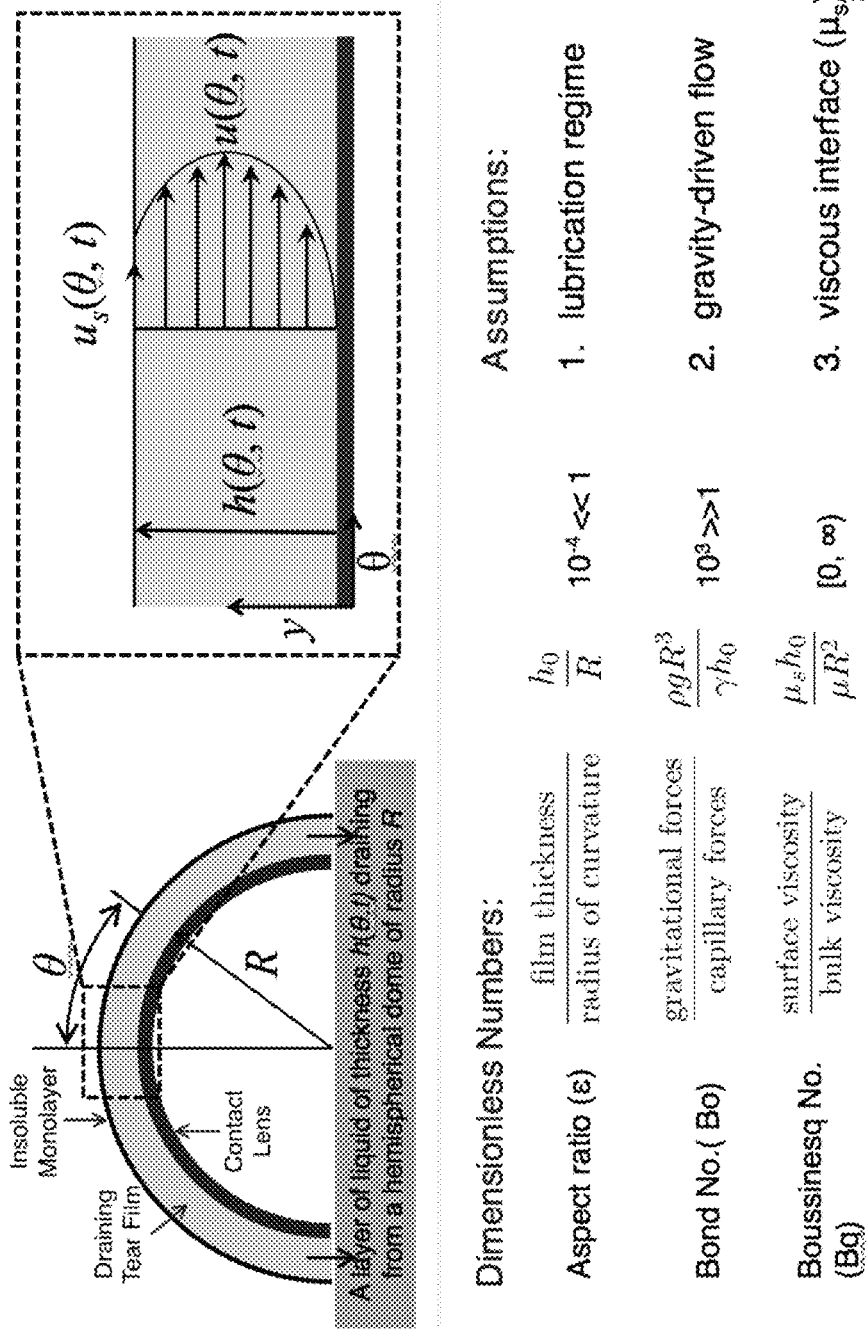
FIG. 3 shows a schematic explaining the mathematical model used to described drainage according to an exemplary embodiment of the invention.

FIG. 3 shows a schematic explaining the mathematical model used to described drainage according to an exemplary embodiment of the invention. The top left shows a hemispherical contact lens on top of which a liquid film is draining. The liquid film has an insoluble monolayer on top of it, which represents the tear film lipids. The dimensionless numbers describe the assumptions and variables that inform the theoretical model. Equations describing the theory for modeling drainage flow are shown in FIG. 4. See also a paper by inventors: Bhamla et al. (2014) entitled "Influence of interfacial rheology on drainage from curved surfaces" and published in Soft Matter, 10(36), 6917-6925. The essence of this theoretical derivation is important in "interpreting" the experimental measurements of thickness information as the films drain.

Figure 5:
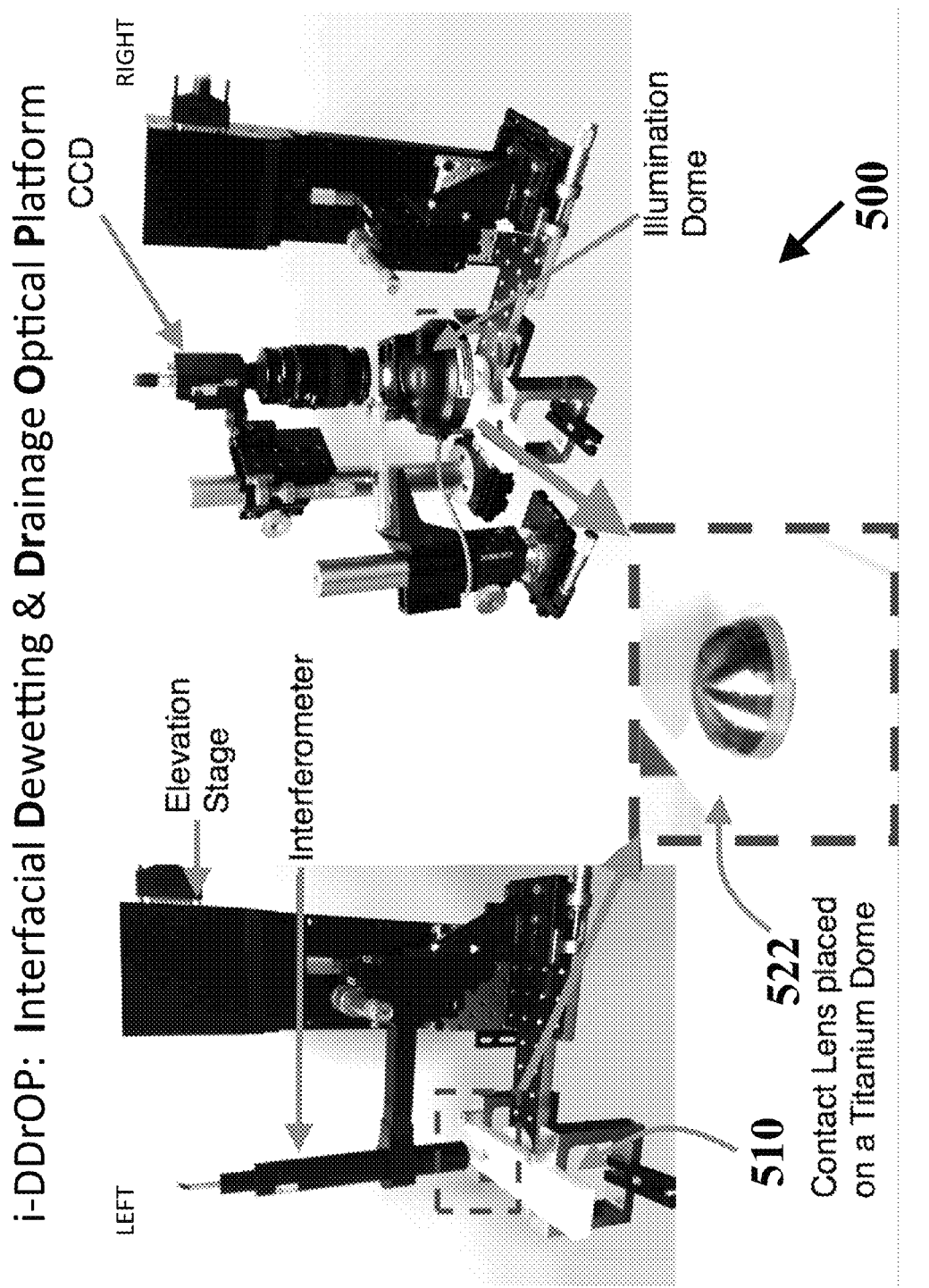
FIG. 5 shows the i-DDrOP (Interfacial Dewetting and Drainage Optical Platform) in two manifestations according to an exemplary to embodiment of the invention.
Figure 6:
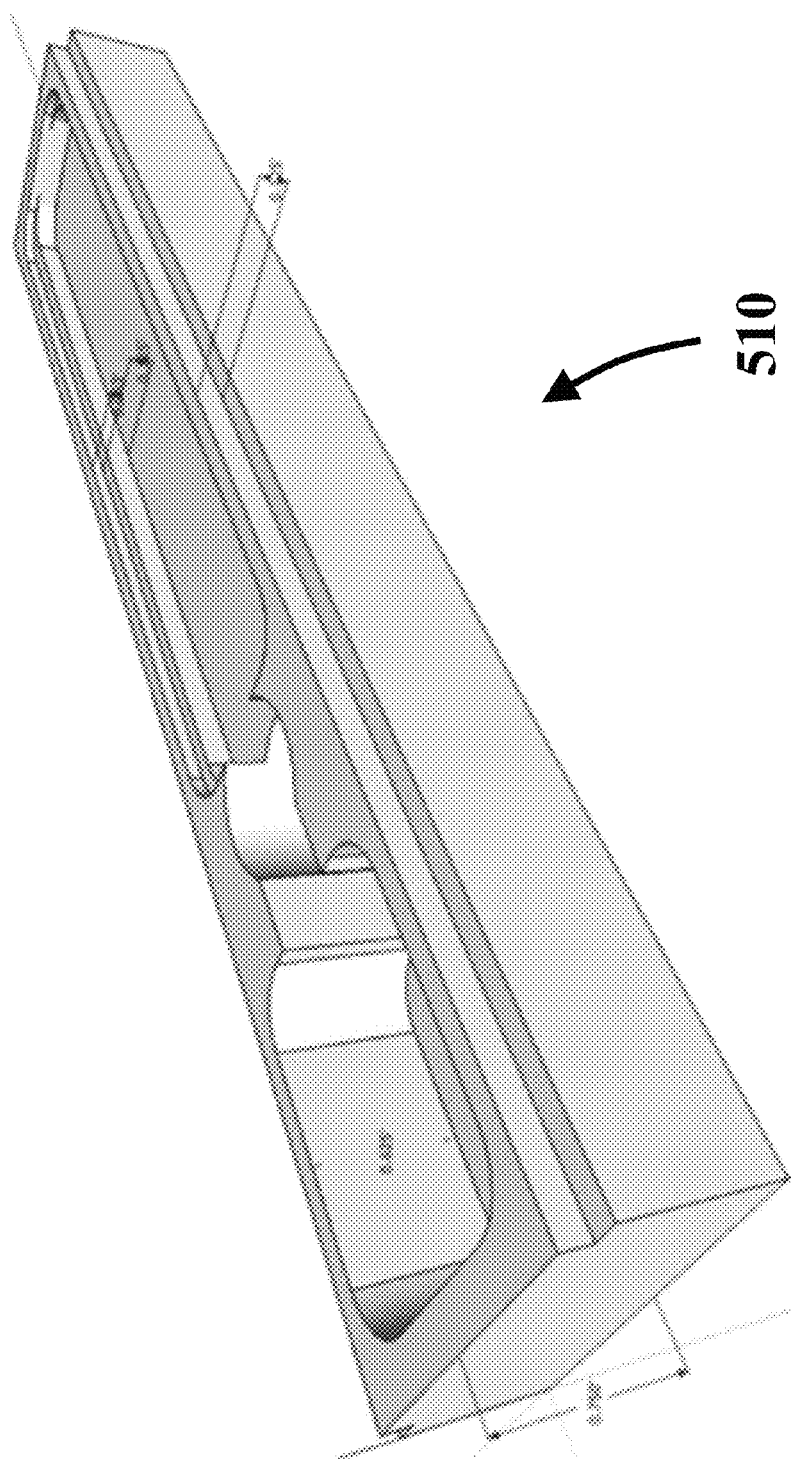
FIGS. 6-7 show a Langmuir trough according to an exemplary embodiment of the invention as a structural component of the i-DDrOP.
Figure 7:
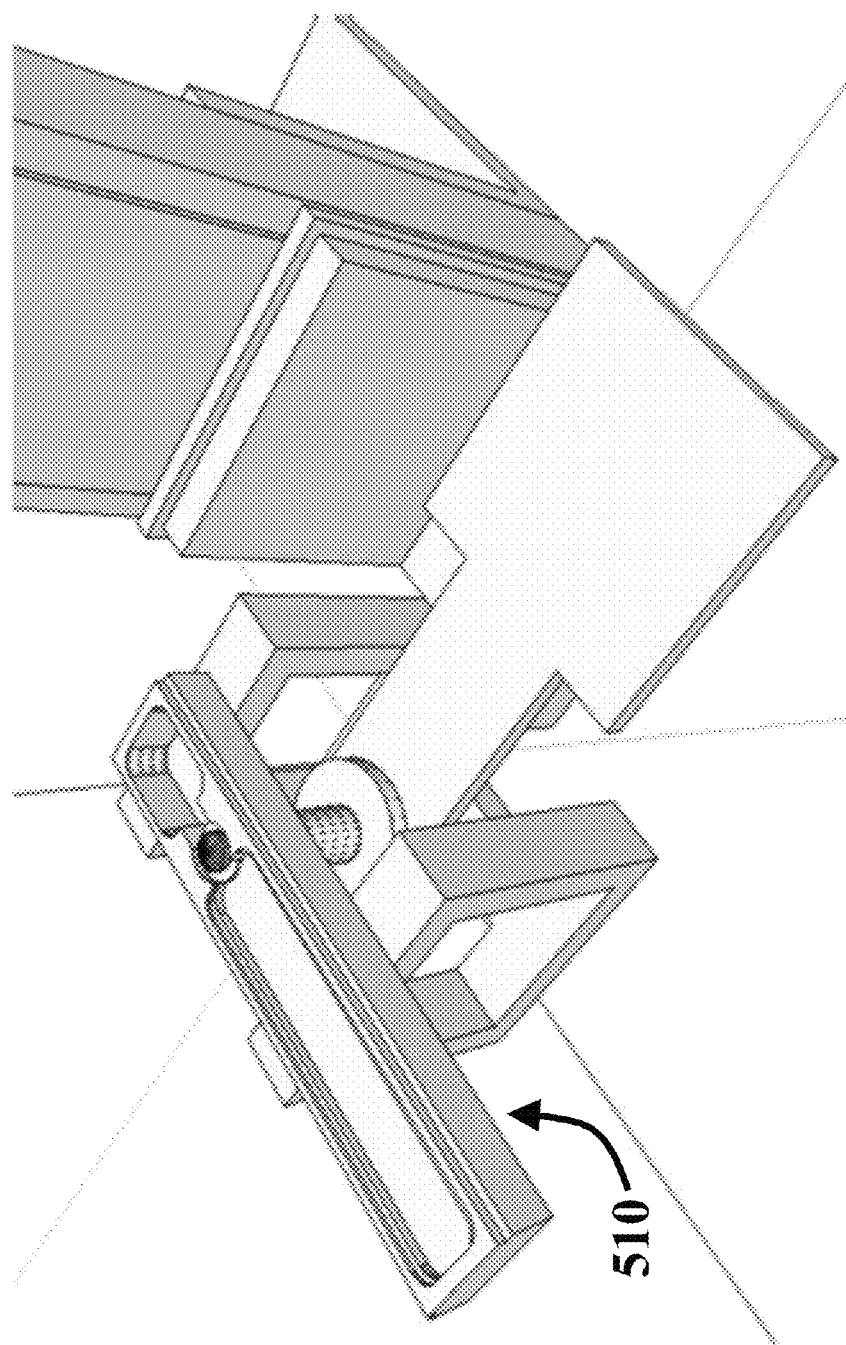
Figure 8:
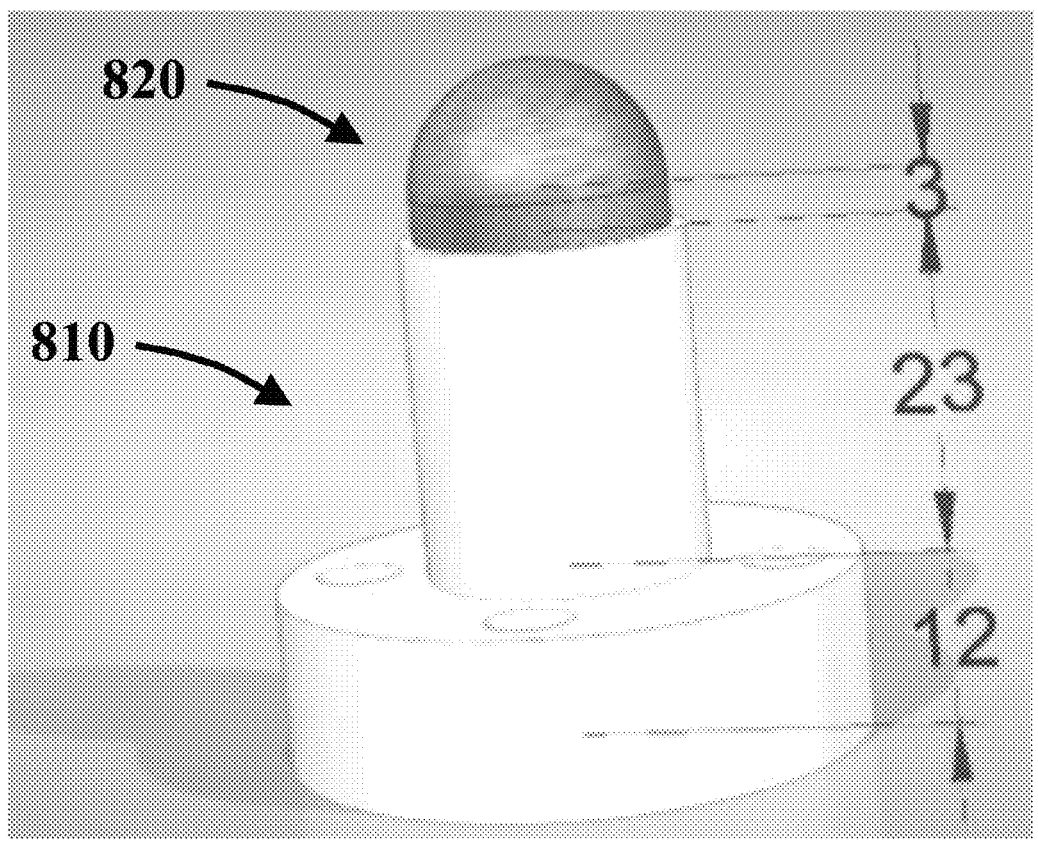
FIG. 8 shows a dome holder with a titanium dome according to an exemplary embodiment of the invention as structural components of the i-DDrOP.
Figure 14:
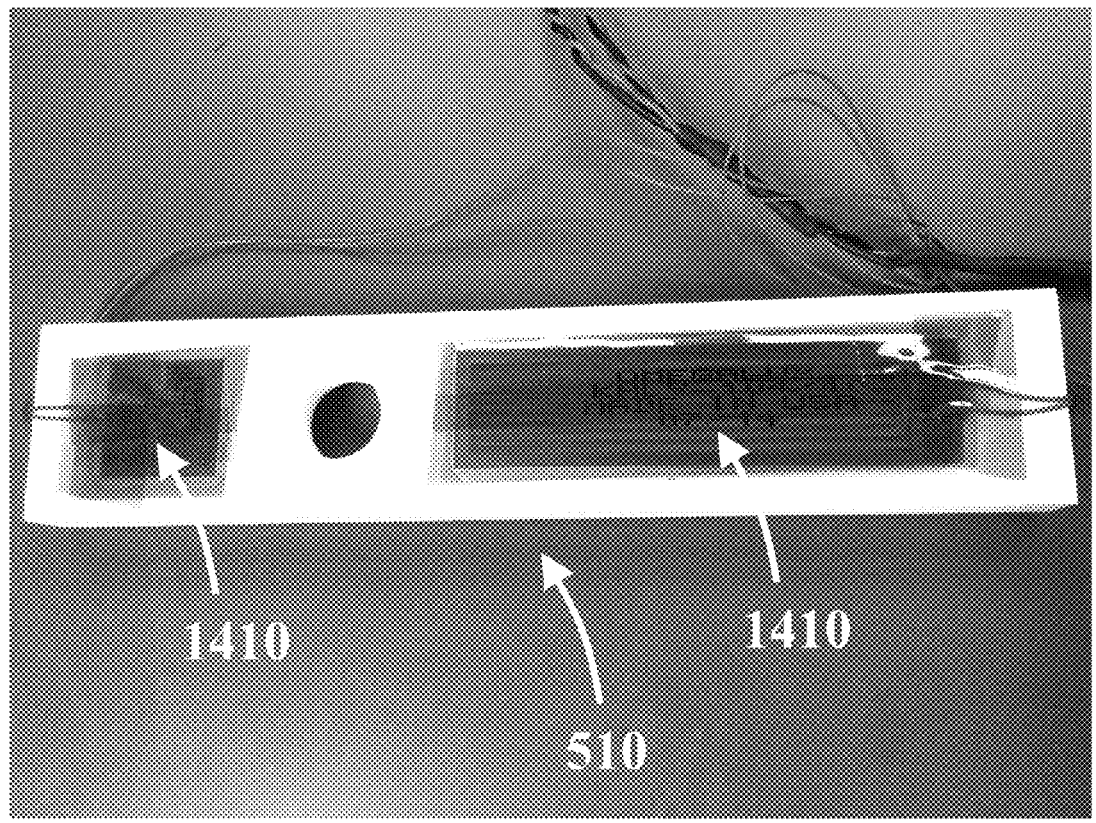
FIG. 14 show according to an exemplary embodiment of the invention heating elements 1410 underneath trough 510.

FIG. 5 shows a photographic example of an i-DDrOP 500, the Interfacial Dewetting and Drainage Optical Platform of this invention in two manifestations. Picture at the left shows the first manifestation of drainage and the picture at the right shows the second manifestation of dewetting. Structural components of the i-DDrOP are:

- A Langmuir trough 510 made of Teflon shown in FIGS. 5-7, which is used for creating a model tear film of an aqueous layer laden with an insoluble Meibomian lipid layer. The trough has heating elements (FIG. 14) on the underside to achieve physiological temperatures for the model in vitro tear film.
- Shown in FIG. 8, a Dome Holder 810 made of Teflon on which a Titanium Dome 820 rests. A contact lens can be placed on top of the Titanium Dome 820. Dome 820 has a diameter of 40 mm and a radius of curvature of 8.6 mm according to one example. There are two versions of the dome. For drainage experiments, a highly polished titanium dome is used. For dewetting experiments a black anodized aluminum dome (to obtain a rough surface) is used.
- Shown in FIG. 5 a high-speed interferometer to measure thickness of the draining films.
- A CCD camera to obtain pictures and/or video of the dome area where the contact lens experiments takes place. The CCD camera is a USB enabled, 1024×768 pixel, high-resolution color camera. A wide-angle macro lens is connected to this CCD camera to achieve the desired depth-of focus imaging and contrast for the dewetting videos.
- A white light LED illumination dome to illuminate the contact lens experiments take place. The illumination dome is a hemisphere with LED lights with a hole at top aligned dome to the CCD camera.
- A computer controlled moving elevation stage for elevating the dome at a wide range of speeds from 0.001-25 mm/s.
- A commercially available surface pressure device to measure the surface pressure of the spread insoluble lipid layers.
- A humidity chamber that allows control over the ambient humidity and temperature.

Figure 9:
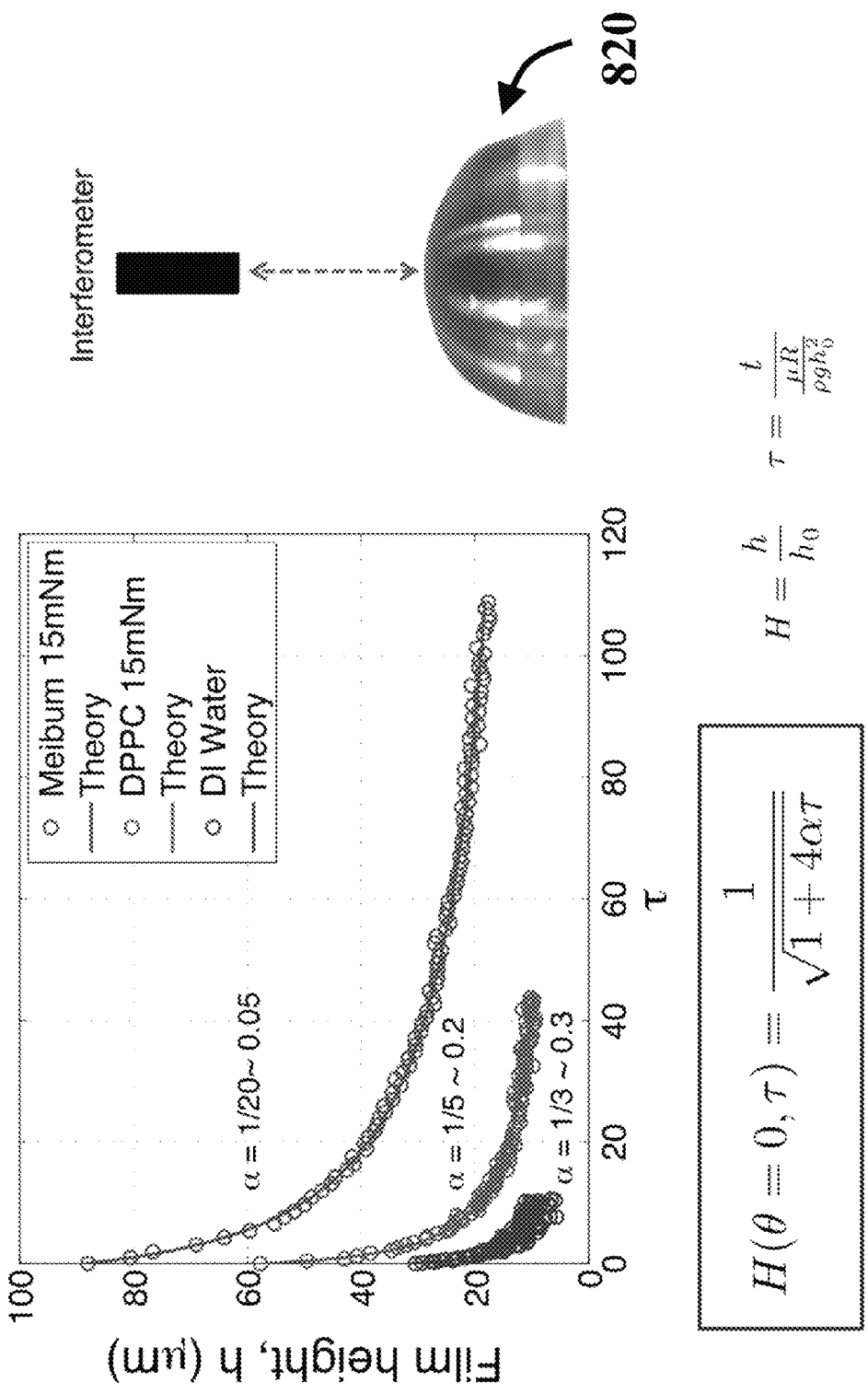
FIG. 9 shows according to an exemplary embodiment of the invention experimental results to measure drainage using the i-DDrOP.

FIG. 9 shows experimental results to measure the effect of drainage on thickness using the i-DDrOP. Specifically, we studied the influence of insoluble surfactant. The experimental data is fitted to the theoretical equation derived in FIG. 4 and shown in the box. The finding in this experiment was that meibum (from tear film) slows down the drainage, which indicates its role as a stabilizing agent on the tear film. Further details of the experiments can be found in the same paper mentioned supra by inventors: Bhamla et al. (2014) entitled "Influence of interfacial rheology on drainage from curved surfaces" and published in Soft Matter, 10(36), 6917-6925.

FIG. 10A-C each showing snapshots of a dewetting experiment on a contact lens using the i-DDrOP. In each of the figures, on the left is a snap shot from a real video obtained with the CCD camera, on the right is a processing version of the video image after running it through a Matlab script (APPENDIX A). The script, as listed infra, uses image analysis algorithms to convert the color CCD video to a black/white digital image. The digitized video frames are then used to quantify the dewetting characteristics as shown in the plot below in each of the figures in FIGS. 10A-C. In this example, dewetting is quantified as a ratio of the dewet area to the total area and is plotted as a function of time.

Figure 11:
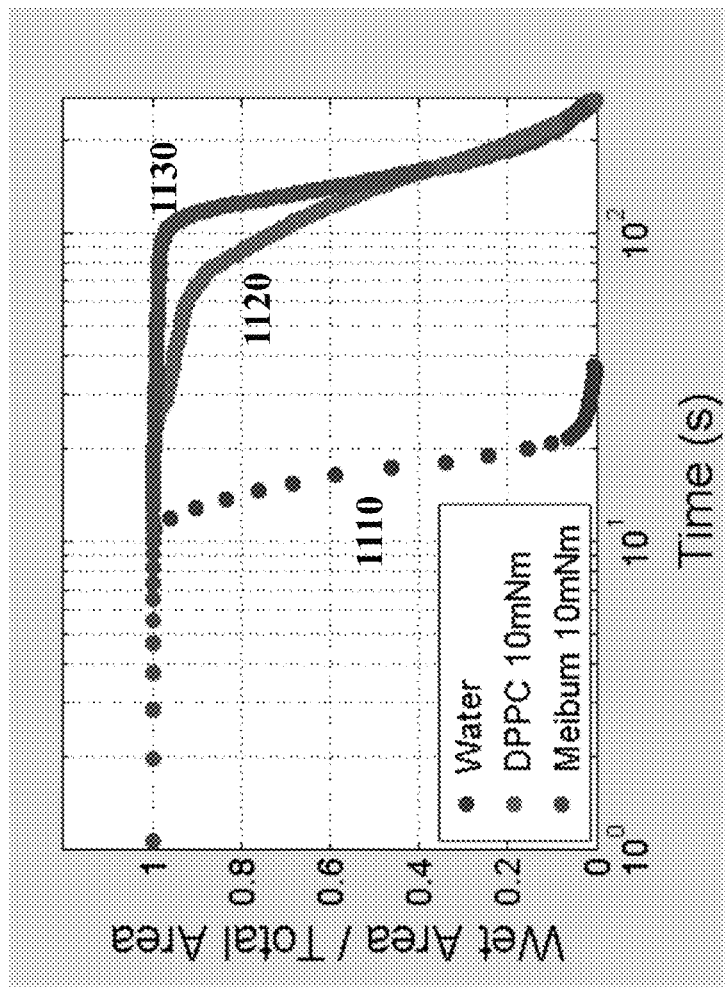
FIG. 11 shows exemplary dewetting results according to an embodiment of the invention.

FIG. 11 shows exemplary dewetting results for three cases: water, DPPC and meibum. From these results it is shown that meibum postpones the onset of dewetting and again, acts as a stabilizing agent for the tear film.

Figure 12:
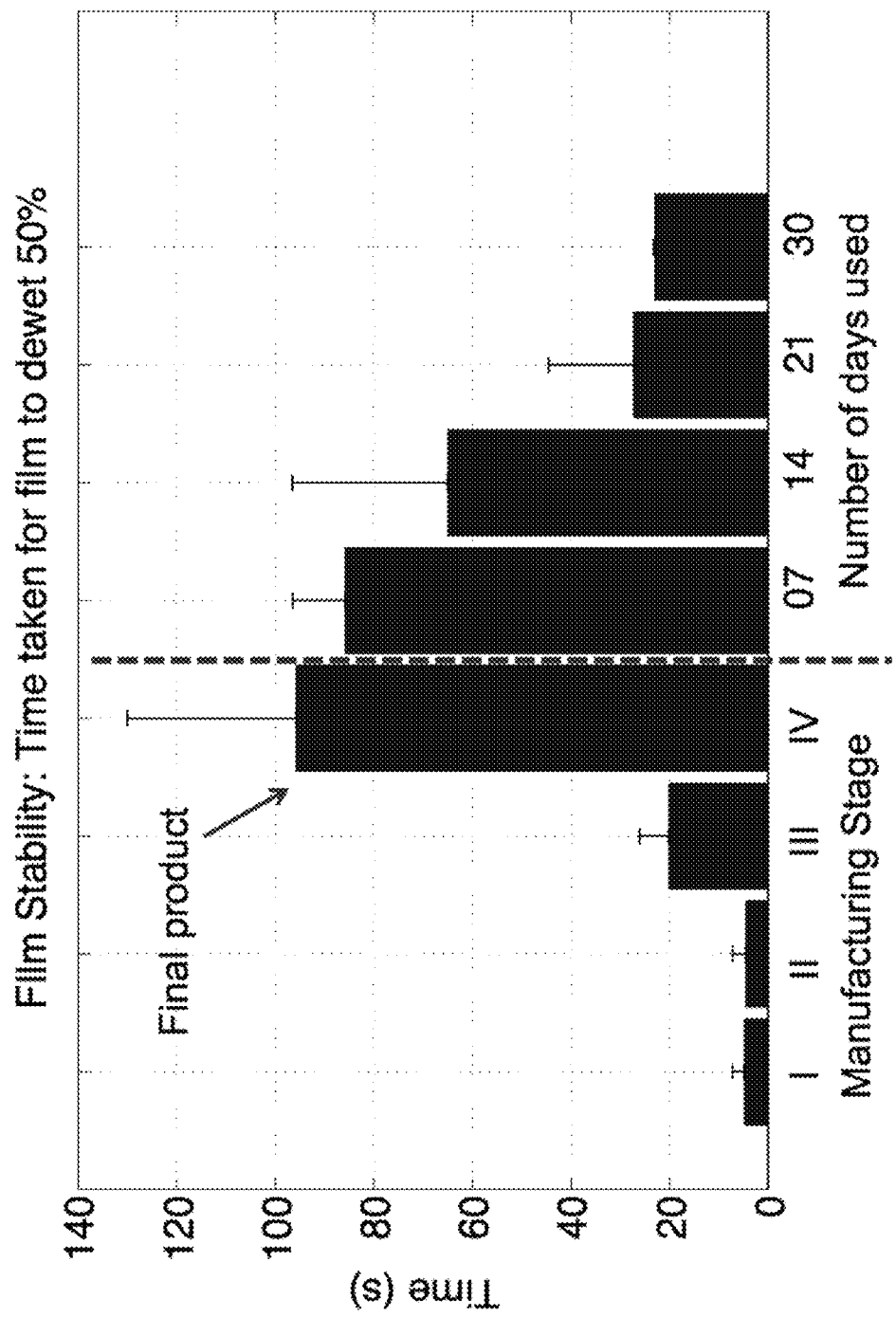
FIG. 12 shows an example dewetting analysis on a commercial contact lens with using the Matlab script as described in APPENDIX A, which is hereby incorporated by reference.
Figure 13:
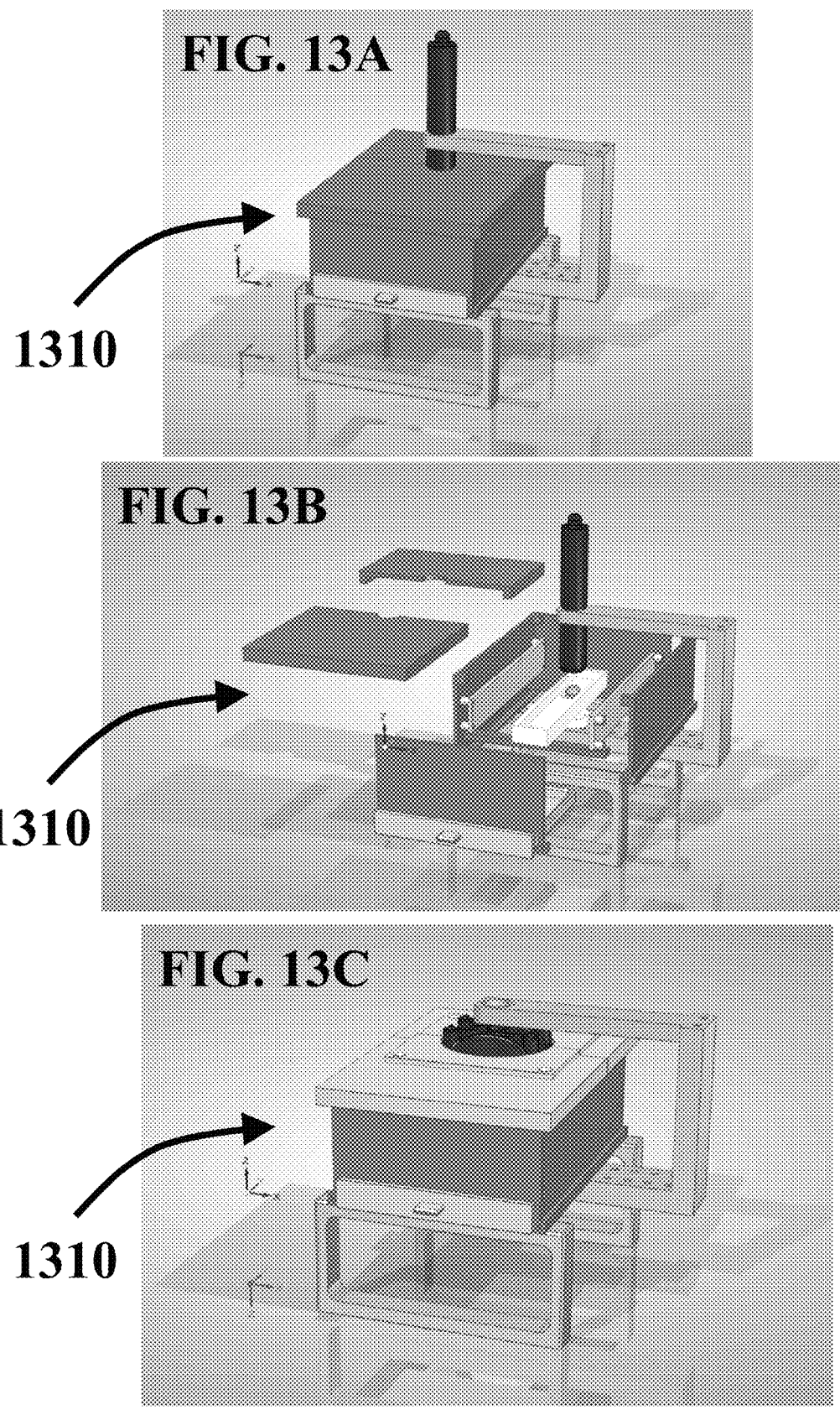
FIGS. 13A-C show according to an exemplary embodiment of the invention a humidity chamber 1310 for the i-DDrOP.

FIG. 12 shows the output of the above-mentioned Matlab script (APPENDIX A). The input to the matlab script is a video file, and the outputs include a digitized B&W video and quantified dewet area ratios as a function of time.

Process of a Drainage Experiment

The trough is thoroughly cleaned with lab-grade ethanol and rinsed with clean water and fixed to the stationary structure as shown in FIG. 7. The dome mount is mounted on the platform. Aqueous solution is filled in the trough. The aqueous solution maybe a buffer solution or an artificial tears solution, depending on the experiment. The dome is raised above the liquid interface and a clean contact lens is placed on it. The dome and contact lens are then lowered till they are submerged in the liquid solution. The surface pressure device is enabled to measure the initial surface pressure. In the case of temperature-controlled experiments, the heating elements are switched on and temperature of the solution monitored till the required temperature is achieved. Insoluble lipid solutions are spread on the air-liquid interface using a micro-syringe and the surface pressure monitored. The lipids are compressed using the movable Teflon barrier till the desired surface pressure is achieved. The mounted interferometer is brought into place till the lens is in focus. The elevation stage is then commanded to elevate at a specific speed till the lens-dome break through the liquid-lipid interface. In this swift upward movement, the lens captures a thin liquid film laden with the lipids, which begins to thin due to gravitational forces. The interferometer moves with the elevation stage and measures the thinning film. Once the film has become thin enough (<30 microns) and beyond the resolution of the interferometer, the experiment is considered completed. The equipment is rinsed out and cleaned for the next experiment. The drainage data is then fitted to the Equation derived in FIG. 4 to interpret the drainage rate.

Process of a Dewetting Experiment

The trough is thoroughly cleaned with lab-grade ethanol and rinsed with clean water and fixed to the stationary structure as shown in FIG. 7. The dome mount is mounted on the platform. Aqueous solution is filled in the trough. The aqueous solution maybe a buffer solution or an artificial tears solution, depending on the experiment. The dome is raised above the liquid interface and a clean contact lens is placed on it. The dome and contact lens are then lowered till they are submerged in the liquid solution. The surface pressure device is enabled to measure the initial surface pressure. In the case of temperature-controlled experiments, the heating elements are switched on and temperature of the solution monitored till the required temperature is achieved. Insoluble lipid solutions are spread on the air-liquid interface using a micro-syringe and the surface pressure monitored. The lipids are compressed using the movable Teflon barrier till the desired surface pressure is achieved. The dome light is rotated into place just above the dome and contact lens. The CCD camera is adjusted till the lens is in focus and the camera, dome light and contact lens are co-aligned along the same vertical axis. The elevation stage is then commanded to elevate at a specific speed till the lens-dome break through the liquid-lipid interface. In this swift upward movement, the lens captures a thin liquid film laden with the lipids, which begins to thin due to gravitational forces and ultimately breaks up and dewets exposing the dry contact lens surface. The CCD camera records this entire process. The experiment is considered complete once the entire exposed lens surface is dry and the film has dewetted. The video file is then passed as an input to the matlab script (APPENDIX A), which converts this information into quantifiable data of dewet/total area ratios as a function of time. The trough is rinsed and thoroughly cleaned for the next experiment Applications i-DDrOP can be used for a variety of experiments such as for example:

Measuring the influence of different substrate contact angles on dewetting. This is useful in comparing different lens coatings or to compare between different commercial lenses. Since the i-DDrOP mimics the dewetting process on the eye, this information would reveal how different contact lenses would interact with the tear film in-vivo.

Revealing the impact of surface tension of the liquid. This is important in the design of artificial tear drops or lens cleaning solutions, whose surface tension needs to be accurately described to ensure no adverse effects on the eye.

Enabling drainage and dewetting studies on contact lenses with artificial tear solutions and not just clean water. For most other devices, clean water is used to test contact lenses. However, for better design of eye care products, it is important to test and understand the interaction of the contact lens with solutions that faithfully mimic the tear film such as an artificial tear solution.

Studying the influence of osmolarity. This is important again for design of cleaning solutions and rewetting drops.

Studying the degradation in quality of the lens after wearing for 7, 14, 21 and 30 days. This information is useful for designing a contact lens.

Studying the contact lens during various stages of its manufacturing and can identify differences between stages. This information is useful for designing a contact lens.

Studying fouling of contact lenses with tear film components. This is important because this device enables controlling fouling which is useful for the study of lens care solutions.

Some aspects of such studies can also be found in the same paper mentioned supra by inventors: Bhamla et al. (2014) entitled "Influence of interfacial rheology on drainage from curved surfaces" and published in Soft Matter, 10(36), 6917-6925.

What is claimed is:

1. A system for analyzing characteristics of a contact lens, comprising:
(a) a Langmuir trough fixed onto a stationary support structure with heating elements, wherein the Langmuir trough allows one to spread an insoluble monolayer of material on top of an aqueous sub-phase at a controlled surface pressure and temperature;
(b) a dome holder supporting a spherical titanium dome capable of supporting the contact lens;
(c) a moving platform for elevating the dome holder, while holding the contact lens on top of the spherical titanium dome, from an initial position slightly beneath the interface of the content in the Langmuir trough and sending the contact lens through the content in the Langmuir trough at computer-controlled speeds;
(d) an interferometer for acquiring thickness data of an aqueous layer on the top of the lens as a function of time;
(e) a color CCD camera for acquiring video data of the contact lens; and
(f) a computer executing a computer-implemented code for analyzing the acquired video data and outputting wettability characteristics of the contact lens.

* * * * *